(12) United States Patent
Park et al.

(10) Patent No.: US 8,945,483 B2
(45) Date of Patent: Feb. 3, 2015

(54) METHOD FOR ATTACHING RFID TAG OF MEMORY CASSETTE FOR TISSUE SPECIMEN AND MEMORY CASSETTE FOR TISSUE SPECIMEN HAVING RFID TAG

(75) Inventors: Byung Gyu Park, Daejeon (KR); Yong Pill Kim, Daejeon (KR); Kwang Il Choi, Daejeon (KR)

(73) Assignee: Time System Co., Ltd., Daejeon (KR)

( * ) Notice: Subject to any disclaimer, the term of this patent is extended or adjusted under 35 U.S.C. 154(b) by 0 days.

(21) Appl. No.: 13/636,491

(22) PCT Filed: Oct. 21, 2010

(86) PCT No.: PCT/KR2010/007248
§ 371 (c)(1),
(2), (4) Date: Sep. 21, 2012

(87) PCT Pub. No.: WO2011/118894
PCT Pub. Date: Sep. 29, 2011

(65) Prior Publication Data
US 2013/0022518 A1    Jan. 24, 2013

(30) Foreign Application Priority Data
Mar. 22, 2010    (KR) .................. 10-2010-0025217

(51) Int. Cl.
*A61B 10/00*    (2006.01)
*A61B 19/00*    (2006.01)

(52) U.S. Cl.
CPC ............ *A61B 10/0096* (2013.01); *A61B 19/44* (2013.01); *A61B 2019/448* (2013.01)
USPC ................. 422/536; 422/63; 422/64; 422/65; 422/66; 422/67

(58) Field of Classification Search
USPC ............................... 422/63–67, 536
See application file for complete search history.

(56) References Cited

U.S. PATENT DOCUMENTS

| | | | |
|---|---|---|---|
| 6,957,777 B1 * | 10/2005 | Huang | .......................... 235/492 |
| 7,179,424 B2 | 2/2007 | Williamson, IV et al. | |
| 7,722,810 B2 | 5/2010 | Allen et al. | |
| 7,776,274 B2 | 8/2010 | Williamson, IV et al. | |
| 7,829,028 B2 | 11/2010 | Elsener | |
| 2005/0084425 A1 | 4/2005 | Williamson, IV et al. | |
| 2005/0147538 A1 | 7/2005 | Williamson, IV et al. | |

(Continued)

*Primary Examiner* — Jyoti Nagpaul
(74) *Attorney, Agent, or Firm* — Rabin & Berdo, P.C.

(57) ABSTRACT

Disclosed are a method for attaching an RFID tag to a memory cassette for tissue specimens and a memory cassette for tissue specimens having the RFID tag attached thereto, in which the RFID tag is attached to the memory cassette for tissue specimens and the RFID tag operates stably even when the memory cassette having the RFID tag attached thereto comes in contact with chemicals or is submerged in various chemical solutions. The method includes forming the memory cassette for tissue specimens provided on an inclined plane of a front surface of a body with an RFID tag insertion groove, inserting the RFID tag into the RFID tag insertion groove provided on the inclined plane of the body, and attaching a protective cap onto the top of the inclined plane of the body in which the RFID tag is inserted into the RFID tag insertion groove, and coupling the protective cap to the inclined plane of the body by ultrasonic welding to adhere the RFID tag to the body of the memory cassette for tissue specimens. Accordingly, the RFID tag can operate stably even when the memory cassette for tissue specimens having the RFID tag attached thereto comes in contact with chemicals or is submerged in chemical solutions or water.

2 Claims, 7 Drawing Sheets

(56) References Cited

U.S. PATENT DOCUMENTS

| | | |
|---|---|---|
| 2005/0226770 A1 | 10/2005 | Allen et al. |
| 2006/0239867 A1* | 10/2006 | Schaeffer .................... 422/102 |
| 2007/0104618 A1 | 5/2007 | Williamson, IV et al. |
| 2007/0205126 A1 | 9/2007 | Elsener et al. |
| 2008/0309497 A1* | 12/2008 | Bryant ...................... 340/572.8 |
| 2011/0121001 A1 | 5/2011 | Elsener et al. |

* cited by examiner

METHOD FOR ATTACHING RFID TAG OF MEMORY CASSETTE FOR TISSUE SPECIMEN AND MEMORY CASSETTE FOR TISSUE SPECIMEN HAVING RFID TAG

TECHNICAL FIELD

The present invention relates to a method for attaching a radio frequency identification (RFID) tag to an apparatus for handling tissue specimens of patients or for tissue specimens for laboratory animal and plant research, and a memory cassette to which the RFID tag is attached. More specifically, the present invention relates to a method for attaching an RFID tag to a memory cassette for tissue specimens, in which the RFID tag is attached to the memory cassette for tissue specimens, and the RFID tag stably operates, although the memory cassette having the RFID tag attached thereto comes in contact with chemicals or is submerged in various chemical solutions, and a memory cassette to which the RFID tag is attached.

BACKGROUND ART

Clinical tissue specimens are considered to be important resources in treatment of diseases or development of novel drugs. In research institutes or medical institutes, tissue specimen samples suitable for specific diseases are managed with the present cases, utilized as important sources to diagnose causes of diseases and stored to verify the subsequent patient disease history. Institutes that perform biopsy of domestic patients should obligatorily store treated specimens for five years or longer. In some cases, the treated specimens should be stored for a long period of time in case of needing research and follow-up examination of patient diseases.

There are cassettes for medical tissue specimens in need of histopathologic examination or for laboratory animal and plant research, as apparatuses for handling tissue specimens of patients or tissue specimens for laboratory animal and plant research. These cassettes are cases made of a synthetic resin material for treating and storing treated tissue specimens.

FIG. 1 is a perspective view illustrating a conventional cassette for tissue specimens. FIG. 2 is a perspective view illustrating a conventional cassette for tissue specimens in which a cover is separated.

As shown in FIGS. 1 and 2, the cassette 10 for tissue specimens includes a body 11 that contains, treats and stores tissue specimens, and a cover 12 detachably mounted on the body 11. The body 11 and the cover 12 are provided with a plurality of rectangular vent holes through which air passes. Also, the body 11 is provided at the front surface thereof with an inclined plane 11a. Identification information of tissue specimens stored inside the body is recorded in the inclined plane 11a.

Tissue specimens in need of pathological examination are contained and stored in the cassette 10 having the configuration. Identification information to exhibit tissue specimen information is recorded in the inclined plane 11a of the cassette 10, in which tissue specimens are stored, and is used to confirm tissue specimen information stored in the cassette 10.

The process for recording identification information in cassettes to exhibit the tissue specimen information is carried out by manual operation or using a cassette printer. A process for matching and confirming tissue specimen information and identification information stored in the process of recording tissue specimen identification information in cassettes is required, thus disadvantageously consuming a long period of time. Also, when the corresponding tissue specimens are examined again or sample tissue specimens are utilized, after the cassettes subjected to examination are stored, identification information recorded in the corresponding cassettes are searched and confirmed one by one in a storage box to identify the corresponding cassettes. For this reason, a long period of time is required for position tracking and information recognition, thus making management difficult. Accordingly, there is a demand for methods for rapidly and easily identifying and managing tissue specimen information stored in cassettes.

DISCLOSURES

Technical Problem

Therefore, the present invention has been made in view of the above problems, and it is one object of the present invention to provide a method for attaching an RFID tag to a memory cassette for tissue specimens, in which the memory cassette is produced by attaching a tissue specimen information-registered RFID tag to the memory cassette for tissue specimens, and, as a result, the RFID tag information is identified using an RFID tag reader, and the RFID tag stably operates although the RFID tag-attached memory cassette contacts chemicals or is immersed in chemical solutions, and a memory cassette for tissue specimens having the RFID tag attached thereto.

Technical Solution

In accordance with one aspect of the present invention, provided is a method for attaching an RFID tag to a memory cassette for tissue specimens of patients in need of histopathologic examination or for tissue specimens for laboratory animal and plant research, the method including: forming the memory cassette for tissue specimens provided on an inclined plane of a front surface of a body with an RFID tag insertion groove; inserting the RFID tag into the RFID tag insertion groove provided on the inclined plane of the body; and attaching a protective cap onto the top of the inclined plane of the body in which the RFID tag is inserted into the RFID tag insertion groove, and coupling the protective cap to the inclined plane of the body by ultrasonic welding to adhere the RFID tag to the body of the memory cassette for tissue specimens.

The ultrasonic welding to couple the protective cap onto the inclined plane in which the RFID tag may be inserted into the RFID tag insertion groove is carried out by holding while supplying ultrasound at a power of 45 W to 50 W for 0.1 seconds to 0.5 seconds.

The method may further include testing an operation state of the RFID tag through a waterproofing test of the RFID tag-attached memory cassette for tissue specimens, after the RFID tag is attached to the inclined plane of the body of the memory cassette for tissue specimens.

In accordance with another aspect of the present invention, provided is an RFID tag attached-memory cassette for tissue specimens for patients in need of histopathologic examination or for tissue specimens for laboratory animal and plant research, including: a body provided on an inclined plane of a front surface thereof with an RFID tag insertion groove; an RFID tag inserted into the RFID tag insertion groove formed on the inclined plane of the body; a protective cap attached onto the top of the inclined plane of the body, in which the RFID tag is inserted into the RFID tag insertion groove, and coupled to the inclined plane of the body through ultrasonic welding to fix the RFID tag on the body of the memory cassette for tissue specimens; and a cover detachably mounted to the top of the body.

The protective cap may be coupled to the body of the memory cassette for tissue specimens through ultrasonic welding performed by holding while supplying ultrasound at a power of 48 W for 0.3 seconds.

A support substrate to support the RFID tag may be provided on the rear surface of the inclined plane of the body to which the RFID tag is attached.

Advantageous Effects

The present invention provides a method for attaching an RFID tag onto a memory cassette for tissue specimens and a memory cassette for tissue specimens having the RFID tag attached thereto, in which the RFID tag is inserted into the inside of an inclined plane of the memory cassette, and a protective cap is coupled to the inclined plane through ultrasonic welding to attach the RFID tag to the inside of the memory cassette, and as a result, the RFID tag stably operates although the RFID tag-attached memory cassette contacts chemicals or is immersed in chemical solutions, and RFID tag information attached to the memory cassette is identified using an RFID tag reader, thereby rapidly and easily obtaining tissue specimen information stored in the memory cassette and more accurately managing data using the tissue specimen information.

BRIEF DESCRIPTION OF THE DRAWINGS

The above and other objects, features and other advantage of the present invention will be more clearly understood from the following detailed description taken in conjunction with the accompanying drawings, in which.

BEST MODE

Hereinafter, preferred embodiments of the present invention will be described with reference to the annexed drawings.

Figure 1:
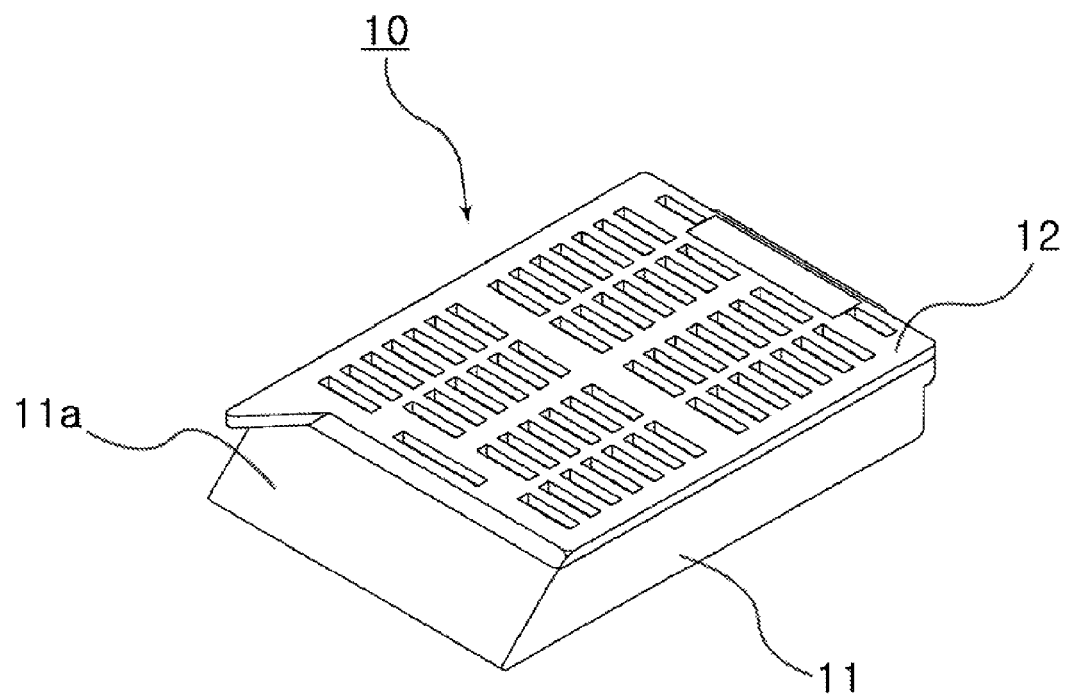
FIG. 1 is a perspective view illustrating a conventional cassette for tissue specimens.
Figure 2:
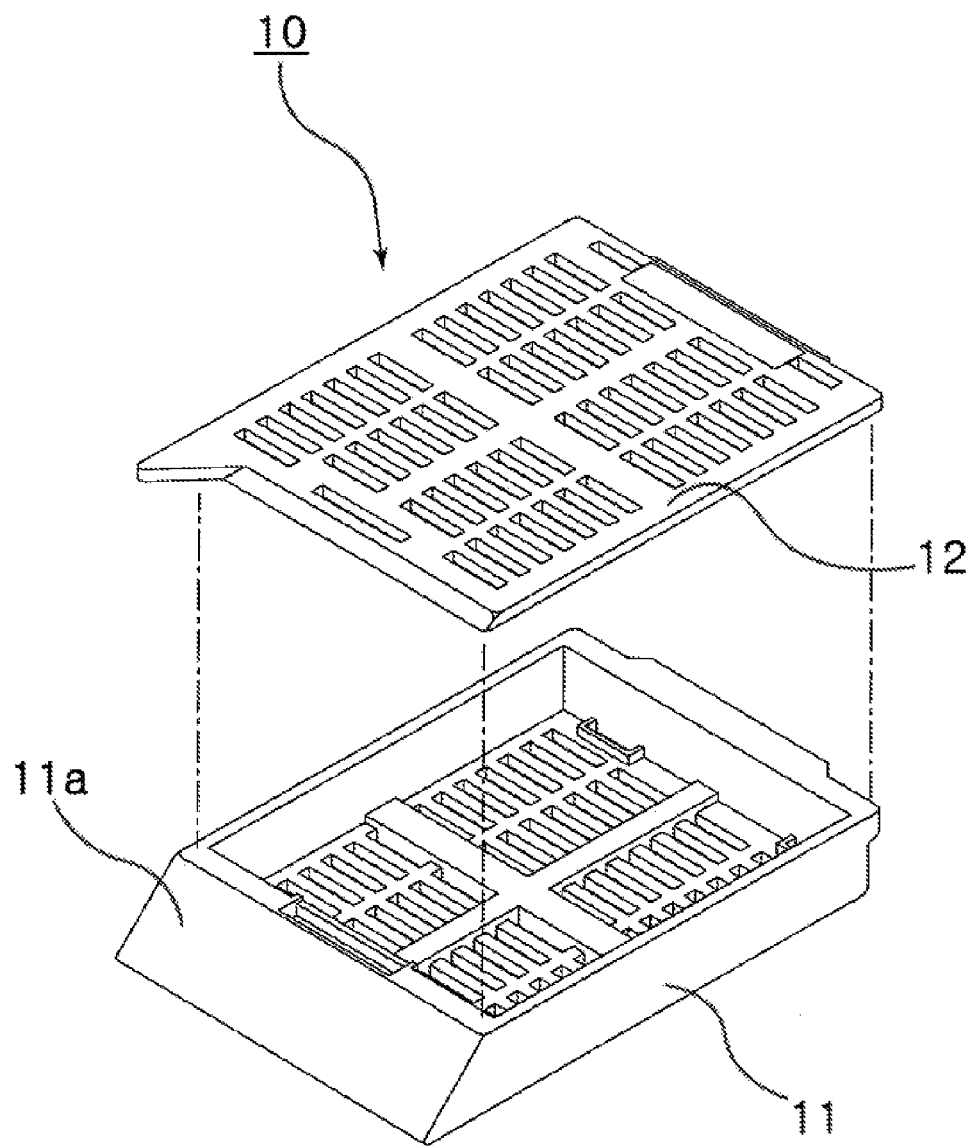
FIG. 2 is a perspective view illustrating a conventional cassette in which a cover is separated.
Figure 3:
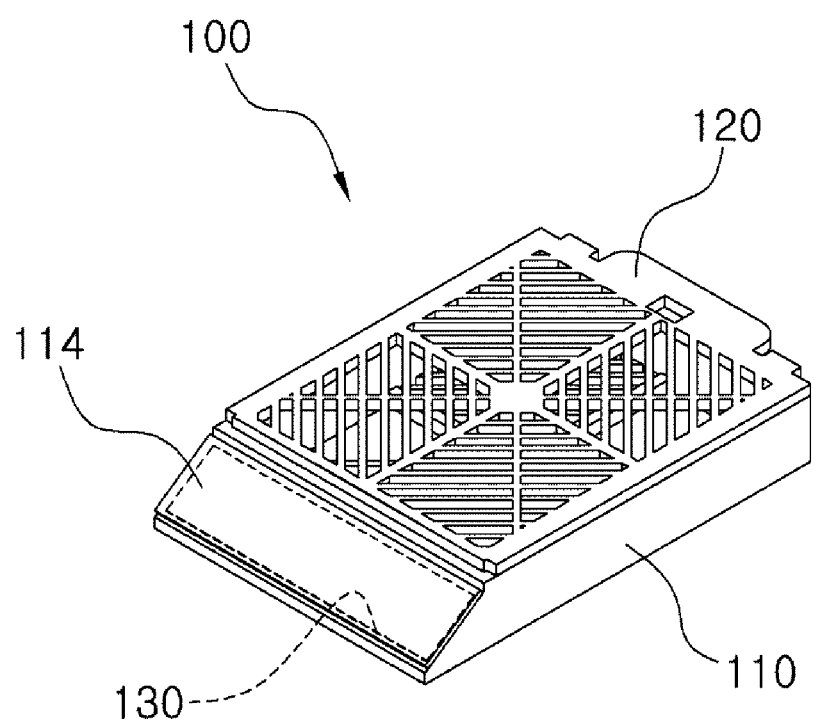
FIG. 3 is a perspective view illustrating an RFID tag-attached memory cassette for tissue specimens according to the present invention.
Figure 4:
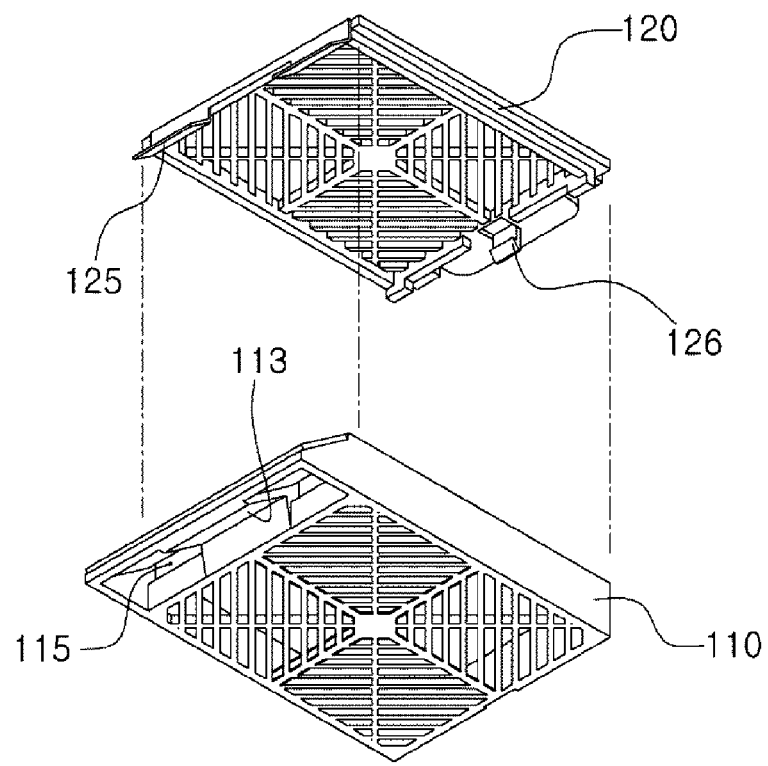
FIG. 4 is a rear perspective view illustrating an RFID tag-attached memory cassette for tissue specimens, in which a cover is separated.
Figure 5:
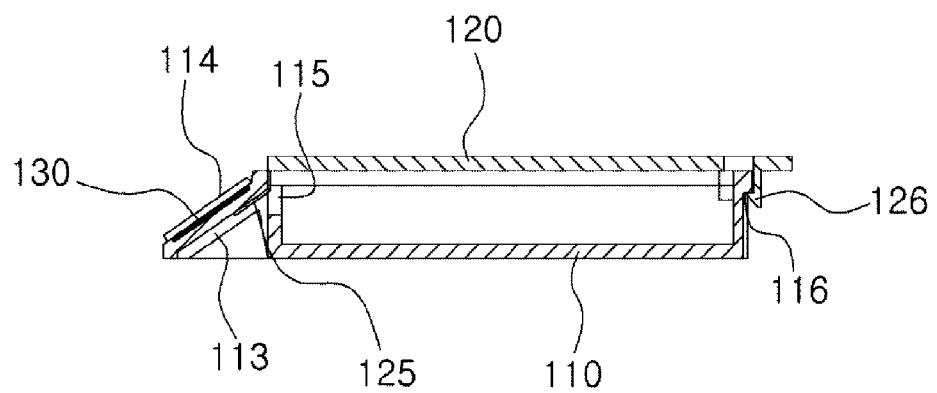
FIG. 5 is a side sectional view illustrating an RFID tag-attached memory cassette for tissue specimens according to the present invention.
Figure 6:
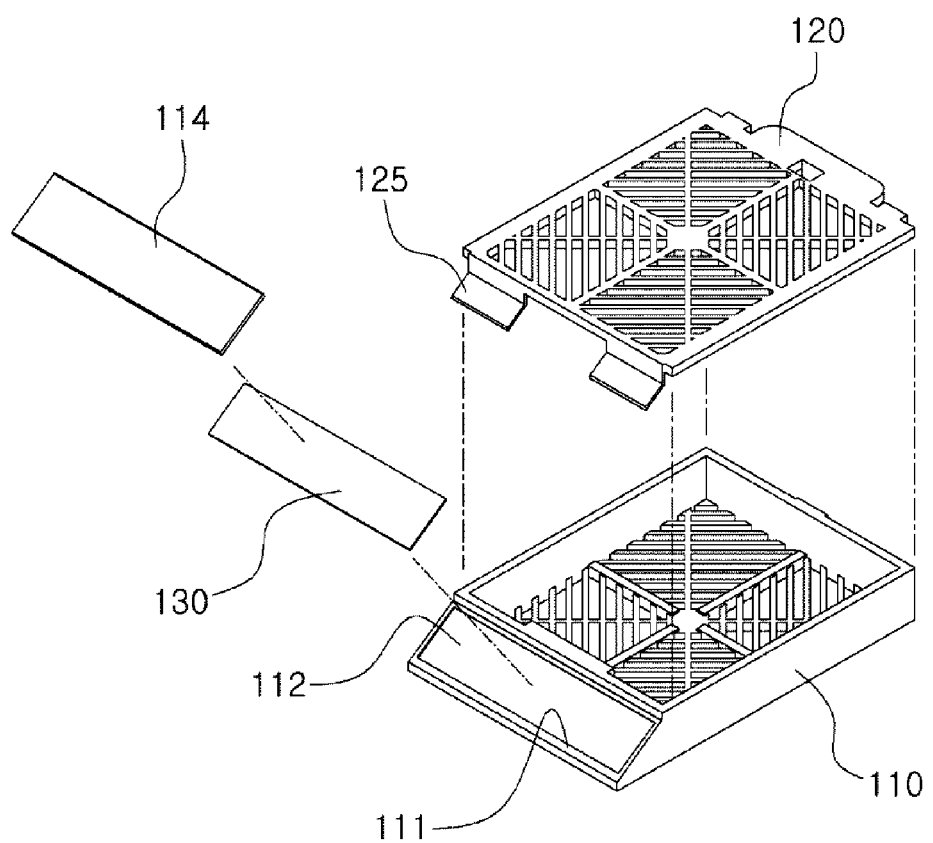
FIG. 6 is an exploded perspective view illustrating an RFID tag-attached memory cassette for tissue specimens according to the present invention.

FIG. 3 is a perspective view illustrating a memory cassette for tissue specimens having an RFID tag attached thereto according to the present invention. FIG. 4 is a rear perspective view illustrating an RFID tag-attached memory cassette for tissue specimens, in which a over thereof is separated, FIG. 5 is a side sectional view illustrating an RFID tag-attached memory cassette for tissue specimens, and FIG. 6 is an exploded perspective view illustrating and RFID tag-attached memory cassette for tissue specimens.

As shown in FIGS. 3 to 6, like general cassettes for tissue specimens, the memory cassette 100 for tissue specimens according to the present invention includes a body 110 having an open top to store tissue specimens therein, and a cover 120 detachably mounted on the top of the body 110.

The bottom of the body 110 and the cover 120 are provided with a plurality of vent holes, through which air passes. In the embodiment of the present invention, the vent holes of the bottom of the body 110 and the cover 120 are radially formed based on the center thereof, thereby preventing the tissue specimens stored therein from being readily discharged and exhibiting visual effects.

The body 110 is provided at the front surface thereof with an inclined plane 111 that is inclined upwardly, a cover coupling groove 115, into which a coupling protrusion 125 provided at the front surface of the cover 120 is inserted and coupled, is provided inside the body 110 on the rear surface of the inclined plane 111, and a cover locking groove 116, on which a locking protrusion 126 provided on the rear surface of the cover 120 is detachably mounted and fixed, is provided on the rear surface of the body 110.

Meanwhile, an RFID tag insertion groove 112, into which the RFID tag 130 is inserted, is provided inside the inclined plane 111 provided at the front surface of the body 110. After the RFID tag 130 is inserted into the RFID tag insertion groove 112 provided on the inclined plane 111 of the body 110, a flat plate-type protective cap 114 is coupled to the top of the inclined plane 111 and the RFID tag 130 is thus coupled to the body of the memory cassette 100.

When the RIFD tag 130 is coupled to the RFID tag insertion groove 112 formed on the inclined plane 111 of the body 110 through the protective cap 114, the RFID tag 130 should be not damaged and a problem associated with operation upon use after coupling should not occur. In particular, since the memory cassette 100 for tissue specimens should be used via a process such as chemical treatment, the RFID tag 130 coupled to the memory cassette 100 should normally operate for a long period of time in chemical solutions or water. For this reason, a method for attaching the RFID tag 130 to the memory cassette 100 is considerably important.

When the RFID tag 130 is coupled to the RFID tag insertion groove 112 formed on the inclined plane 111 of the body 110 through the protective cap 114, the RFID tag 130 should be not damaged and a problem associated with operation upon use after coupling should not occur. In particular, since the memory cassette 100 for tissue specimens should be used via a process such as chemical treatment, the RIFD tag 130 coupled to the memory cassette 100 should normally operate for a long period of time in chemical solutions or water. For this reason, a method for attaching the RFID tag 130 to the memory cassette 100 is considerably important.

In the embodiment of the present invention, after the RFID tag 130 is inserted into the RFID tag insertion groove 112 of the inclined plane 111 of the body, a protective cap 114 is attached onto the top of the RFID tag 130-inserted inclined plane 111, and the protective cap 114 is coupled to the inclined plane 111 by ultrasonic welding. That is, when the RFID tag 130 is inserted into the RFID tag insertion groove 112 formed on the inclined plane 111 of the body 110, the protective cap 114 is attached onto the top of the RFID tag 130-inserted inclined plane 111, and the resulting structure is held, while ultrasound is applied to the protective cap 114 for a predetermined period of time, to couple the protective cap 114 to the inclined plane 111 of the body 110 and thereby stably attach the RFID tag 130 to the RFID tag insertion groove 112 disposed on the inclined plane 111 of the body 110 and inside the protective cap 114. In the embodiment of the present invention, ultrasonic welding to couple the protective cap 114 to the top of the inclined plane 111 is carried out by holding while supplying ultrasound thereto at a power of 45 W to 50 W for 0.1 seconds to 0.5 seconds, more preferably, at a power of 48 W for 0.3 seconds. When ultrasonic welding is carried out under these conditions, the protective cap 114 is stably coupled to the inclined plane 111, and the RFID tag 130 present inside is attached to the inside of the inclined plane 111 and is stably operated.

Meanwhile, a support substrate 113 to stably support the RFID tag 130 inserted into the RFID tag insertion groove 112 is provided in the center on the rear surface of the inclined plane 111 of the body. The support substrate 113 prevents a phenomenon in which the RFID tag 130 inserted into the RFID tag insertion groove 112 is pulled backward or bent and is thus deformed by pressure applied during ultrasonic welding, due to large thickness of the center on the rear surface of the inclined plane 111.

Hereinafter, the memory cassette for tissue specimens having an RFID tag attached thereto having the configuration will be described.

Figure 7:
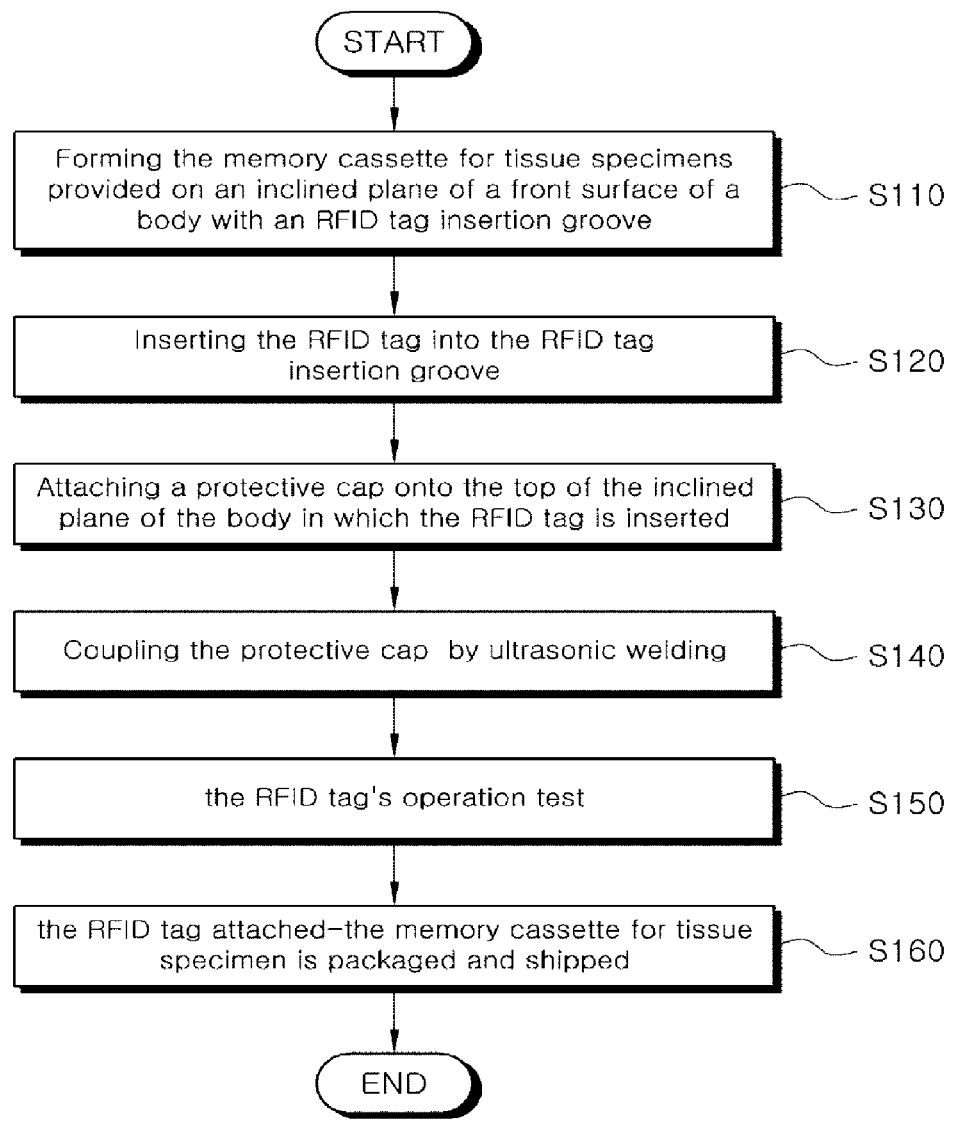
FIG. 7 is a flowchart illustrating a process for attaching an RFID tag to the memory cassette for tissue specimens according to the present invention.

FIG. 7 is a flowchart illustrating a process for attaching an RFID tag to a memory cassette for tissue specimens according to one embodiment of the present invention.

Figure 8:
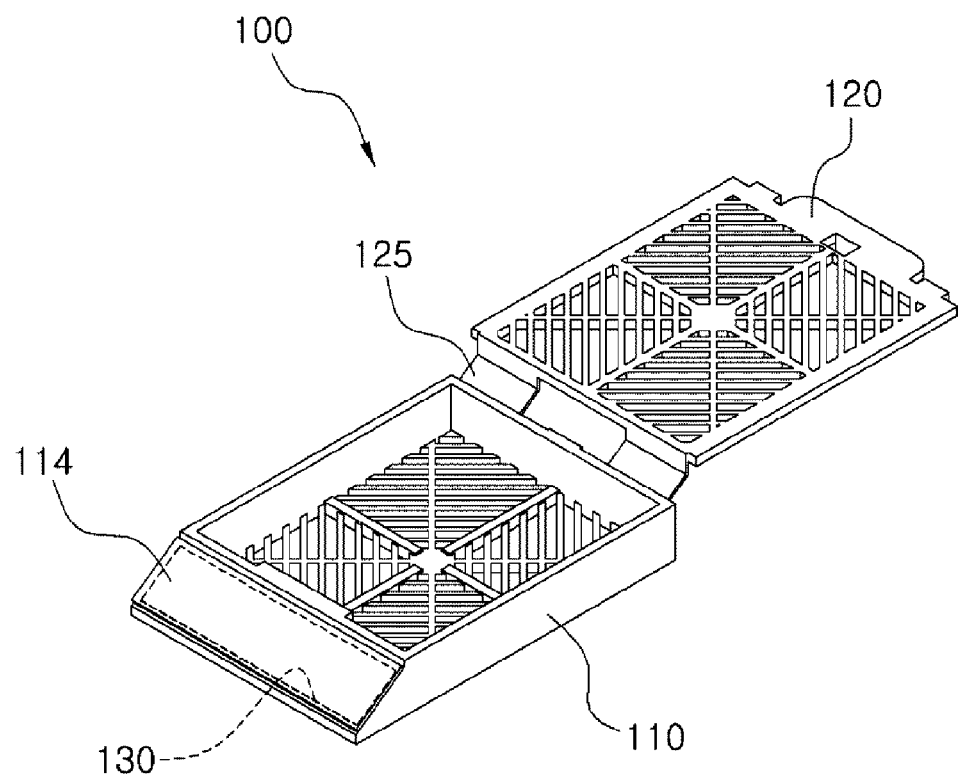
FIG. 8 is a perspective view illustrating a memory cassette for tissue specimens formed according to the present invention.

Step S110: first, for attachment of the RFID tag 130, a body 110 of the memory cassette 100 for tissue specimens provided on an inclined plane 111 of the body 110 with an RFID tag insertion groove 112 and a cover 120 thereof are formed. In the initial production stage of the memory cassette 100 for tissue specimens, the body 110 is integrated with the cover 120. FIG. 8 is a perspective view illustrating the memory cassette for tissue specimens formed according to one embodiment of the present invention. As shown in FIG. 8, the body 110 and the cover 120 are integrally formed in the memory cassette 100 for tissue specimens, but they are used in such a manner that the cover 120 is separated from the body 110 and the cover 120 is coupled to the body 110. In the embodiment of the present invention, the body 110 of the memory cassette 100 for tissue specimens is formed to have a width, a length and a height of 28 mm, 4 mm and 7 mm, respectively. The process for forming the memory cassette 100 for tissue specimens is in accordance with a conventional injection molding method.

Step S120: After the memory cassette 100 for tissue specimens is formed, an RFID tag 130 is inserted into the RFID tag insertion groove 112 formed on the inclined plane 111 of the body 110 to attach the RFID tag 130 to the body 110. The RFID tag 130 applied to the embodiment of the present invention uses a frequency range of 840 to 960 MHz, a memory capacity of 512 bits, and a protocol of ISO18000-6C GEN2. When a recognition distance is fixed, an RFID tag having a distance of 30 cm is used. In case of a handheld RFID tag, an RFID tag having a distance of 5 to 10 cm is used. Examples of these RFID tags include Hix3 produced by Alien Corp., NXP models produced by Philips Co., Ltd, and the like.

Steps S130 and S140: a flat-plate protective cap 114 is attached onto the top of the inclined plane 111 in which the RFID tag 130 is inserted into the RFID tag insertion groove 112 (S130), the protective cap 114 brings in contact with the inclined plane 111, followed by holding, ultrasound is applied thereto, and, as a result, the protective cap 114 is welded and coupled to the inclined plane 111 (S140). In the embodiment of the present invention, application of ultrasound to the protective cap 114 that is attached onto the inclined plane 111 is carried out at a power 45 W to 50 W for a holding time of 0.1 seconds to 0.5 seconds, more preferably, at a power of 48 W for a holding time of 0.3 seconds from viewpoints of breakage prevention and stable welding of the RFID tag 130.

Step S150: when the protective cap 114 is coupled to the inclined plane 111 of the body though this process, whether the RFID tag 130 coupled to the RFID tag insertion groove 112 through the protective cap 114 normal operates is tested. The testing of the RFID tag 130 is carried out by confirming whether the RFID tag 130 is normally recognized using an RFID tag reader and confirming whether the RFID tag 130 is normally recognized during a waterproofing test through precipitation of chemical solutions in water. In the embodiment of the present invention, presence of abnormality is determined by confirming normal operation of the RFID tag 130-attached memory cassette 100 for tissue specimens after immersing the memory cassette 100 in a solution of formalin and xylene for four hours or longer.

Step S160: as a test result, when the RFID tag 130 is determined to normally operate, the RFID tag 130-attached the memory cassette 100 for tissue specimens is packaged and shipped, which is then used in the related field.

In the RFID tag 130-attached memory cassette 100 thus produced through these steps, the RFID tag 130 is stably attached to the memory cassette 100 by ultrasonic welding. For this reason, the memory cassette 100 normally operates when exposed to chemicals or chemical solutions, or water. Accordingly, tissue specimens stored in the memory cassette 100 can be easily managed.

Information registered in the RFID tag 130 of the memory cassette 100 is linked with tissue specimen information stored in the memory cassette 100 and is registered and managed in a database server. Afterwards, when the tissue specimen information is searched or tissue specimens are re-searched, or recycled, information associated with tissue specimens can be rapidly and accurately obtained. That is, the RFID tag 130 information attached to the memory cassette 100 is identified through the RFID tag reader to obtain information of the corresponding tissue specimens. When the RFID tag 130 information of the memory cassette 100 is obtained, detailed information of tissue specimens associated therewith is also obtained. As a result, a manager can rapidly and accurately obtain tissue specimen information. Also, information of storage position of the memory cassette 100 is managed to be interlinked with the corresponding tissue specimen information, to easily confirm the storage position of the memory cassette 100.

The RFID tag 130-attached memory cassette 100 according to the present invention enables rapid and easy management of tissue specimens stored in the memory cassette 100.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

Industrial Applicability

The memory cassette for tissue specimens having an RFID tag attached thereto according to the present invention has a structure in which an RFID tag is stably coupled to the inside of an inclined plane of the memory cassette, to rapidly and accurately obtain tissue specimen information stored in the RFID tag through an RFID tag reader. Accordingly, the present memory cassette is expected to be widely used, instead of conventional memory cassettes in research institutes or medical institutes storing tissue specimens of patients.

What is claimed is:

1. An RFID tag attached-memory cassette for tissue specimens, comprising:
   a body having a plurality of vent holes in a bottom thereof and including a cover locking groove in a first side thereof and a cover coupling groove in a second side thereof, the body storing tissue specimens therein;
   an inclined plane provided in the second side of the body and having an inner surface facing a wall of the body and an outer surface being a reverse surface of the inclined plane;
   a cover mounted on a top of the body and having a plurality of vent holes, the cover being separable from the body and including a locking protrusion provided in a first side of the cover and a coupling protrusion provided in a second side of the cover, the locking protrusion being coupled to the cover locking groove of the body, and the coupling protrusion being coupled to the cover coupling groove of the body;
   an RFID tag insertion groove provided in the outer surface of the inclined plane of the body;
   an RFID tag inserted into the RFID tag insertion groove;
   a support substrate provided on the inner surface of the inclined plane and supporting the inclined plane; and
   a protective cap separated from the RFID tag and coupled to a top of the inclined plane of the body.

2. The RFID tag attached-memory cassette according to claim 1, wherein the protective cap is coupled by a ultrasonic welding performed by supplying an ultrasound at a power of 48 W for 0.3 seconds.

* * * * *